US00PP35187P2

(12) United States Plant Patent
Heemskerk

(10) Patent No.: US PP35,187 P2
(45) Date of Patent: May 23, 2023

(54) ***ERYNGUIM* PLANT NAMED 'LEGMAVI'**

(50) Latin Name: *Eryngium alpinum*
Varietal Denomination: LEGMAVI

(71) Applicant: Pieter Heemskerk, Noordwijkerhout (NL)

(72) Inventor: Pieter Heemskerk, Noordwijkerhout (NL)

( * ) Notice: Subject to any disclaimer, the term of this patent is extended or adjusted under 35 U.S.C. 154(b) by 0 days.

(21) Appl. No.: 17/803,795

(22) Filed: Nov. 28, 2022

(51) Int. Cl.
*A01H 5/02* (2018.01)
*A01H 6/06* (2018.01)

(52) U.S. Cl.
USPC ..... Plt./361
CPC ..... *A01H 6/06* (2018.05)

(58) Field of Classification Search
USPC ..... Plt./361
CPC ..... A01H 6/06; A01H 5/02
See application file for complete search history.

*Primary Examiner* — Keith O. Robinson
(74) *Attorney, Agent, or Firm* — Samuel R. McCoy, Jr.

(57) ABSTRACT

'LEGMAVI' is a new and distinctive variety of *Eryngium alpinum* plant which is characterized by precocious, first-year flowering, continuous flowering throughout the growing season, inflorescences with prominent violet-blue involucres subtending each of the dark blue capitular umbel. The new variety propagates successfully by stem cuttings and tissue culture and has shown to be uniform and stable in the resulting generations from asexual propagation.

3 Drawing Sheets

Latin name of the genus and species: The Latin name of the genus and species of the novel variety disclosed herein is *Eryngium alpinum.*

Variety denomination: The inventive variety of *Eryngium* hybrid disclosed herein has been given the variety denomination 'LEGMAVI'.

BACKGROUND OF THE INVENTION

Parentage: 'LEGMAVI' is a seedling selection resulting from the open pollination of a cultivated population of unnamed *Eryngium alpinum* plants (unpatented). The exact parentage is unknown. In the summer of 2013, seeds were harvested from a plurality of cultivated *Eryngium alpinum* plants and were subsequently germinated and grown to a mature size at a plant nursery in Noordwijkerhout, the Netherlands. A plurality of seedlings from said cross were observed to exhibit precocious flowering and were isolated for further evaluation in order to assess other characteristics such as vigor and aesthetics. In the summer of 2014, one seedling was observed to be superior to all other early-flowering seedlings.

Asexual Reproduction: Asexual reproduction of 'LEGMAVI' was first accomplished in the autumn of 2014 by way of vegetative division at the inventor's plant nursery in Noordwijkerhout, the Netherlands and later by way of meristematic tissue culture micro propagation. Seven successive generations have shown that the unique features of the instant cultivar are stable and reproduce true to type.

SUMMARY OF THE INVENTION

The cultivar 'LEGMAVI' has not been observed under all possible environmental conditions and the phenotype may vary somewhat with variations in the instant environment such as temperature, day length, and light intensity, without, however, any variance in genotype. The following traits have been repeatedly observed and represent the distinguishing characteristics of the new *Eryngium* cultivar, 'LEGMAVI'.

1. *Eryngium* 'LEGMAVI' does not require vernalization to induce flowering; and
2. *Eryngium* 'LEGMAVI' exhibits precocious flowering, blooming in the first year after planting; and
3. *Eryngium* 'LEGMAVI' exhibits continuous flowering and a higher yield of flowering stems in cut flower production; and
4. *Eryngium* 'LEGMAVI' exhibits cauline leaves nearest to the involucre which are heavily suffused with violet-blue; and
5. *Eryngium* 'LEGMAVI' exhibits prominent involucres, with vibrant violet-blue bracts, subtending each umbel; and
6. *Eryngium* 'LEGMAVI' exhibits capitular umbels with a dark blue general coloration.

BOTANICAL DESCRIPTION OF THE PLANT

Figure 1:
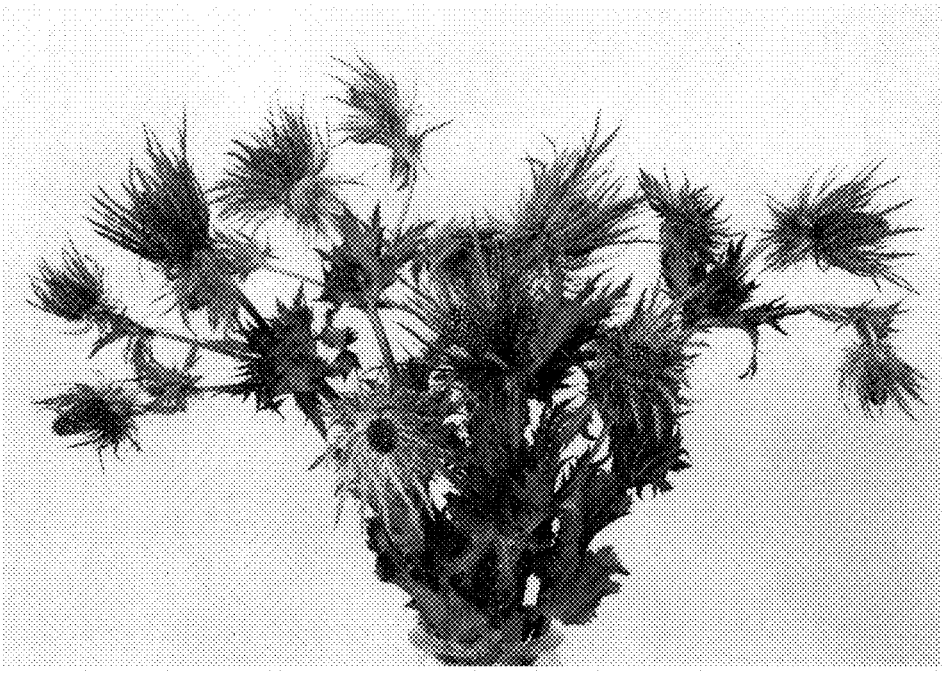
FIG. 1 shows, as nearly true as it is reasonably possible to make the same in color illustrations of this type, the typical flowering stems of the new cultivar, 'LEGMAVI'.
Figure 2:
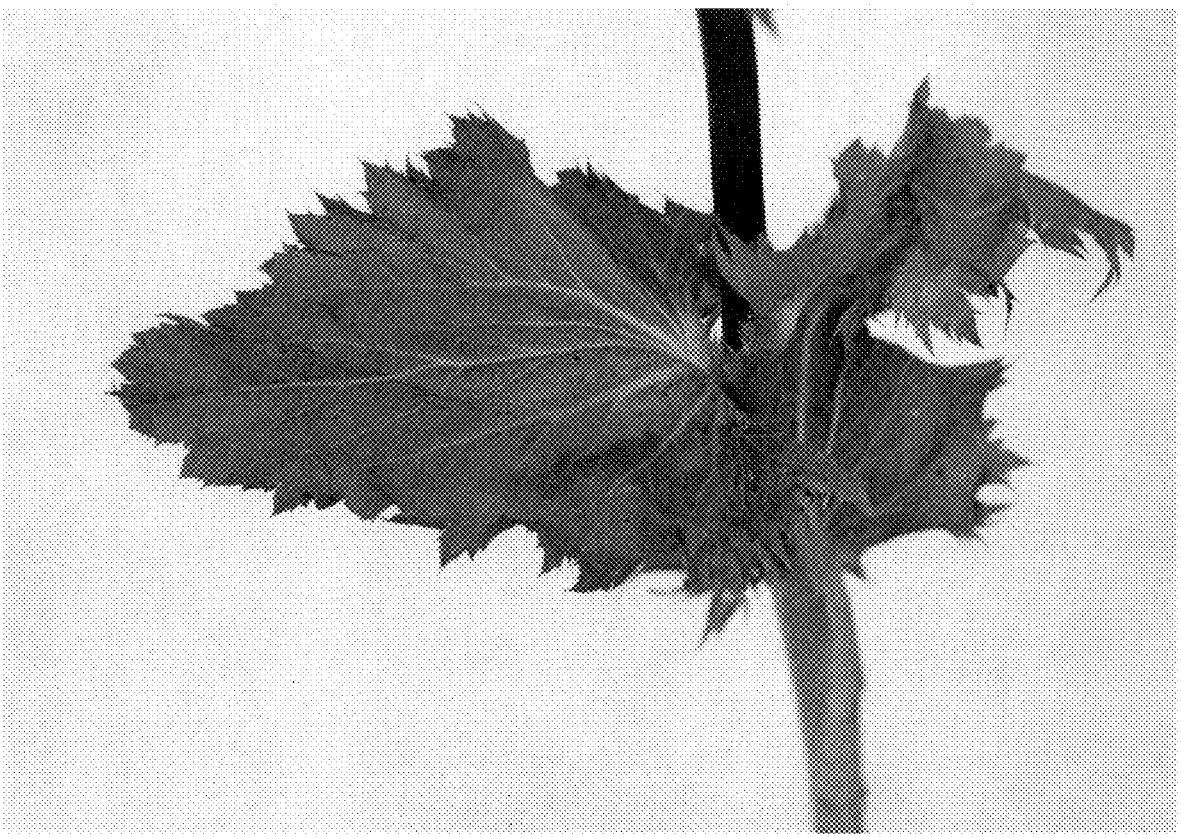
FIG. 2 shows, as nearly true as it is reasonably possible to make the same in color illustrations of this type, the typical foliage of 'LEGMAVI'.
Figure 3:
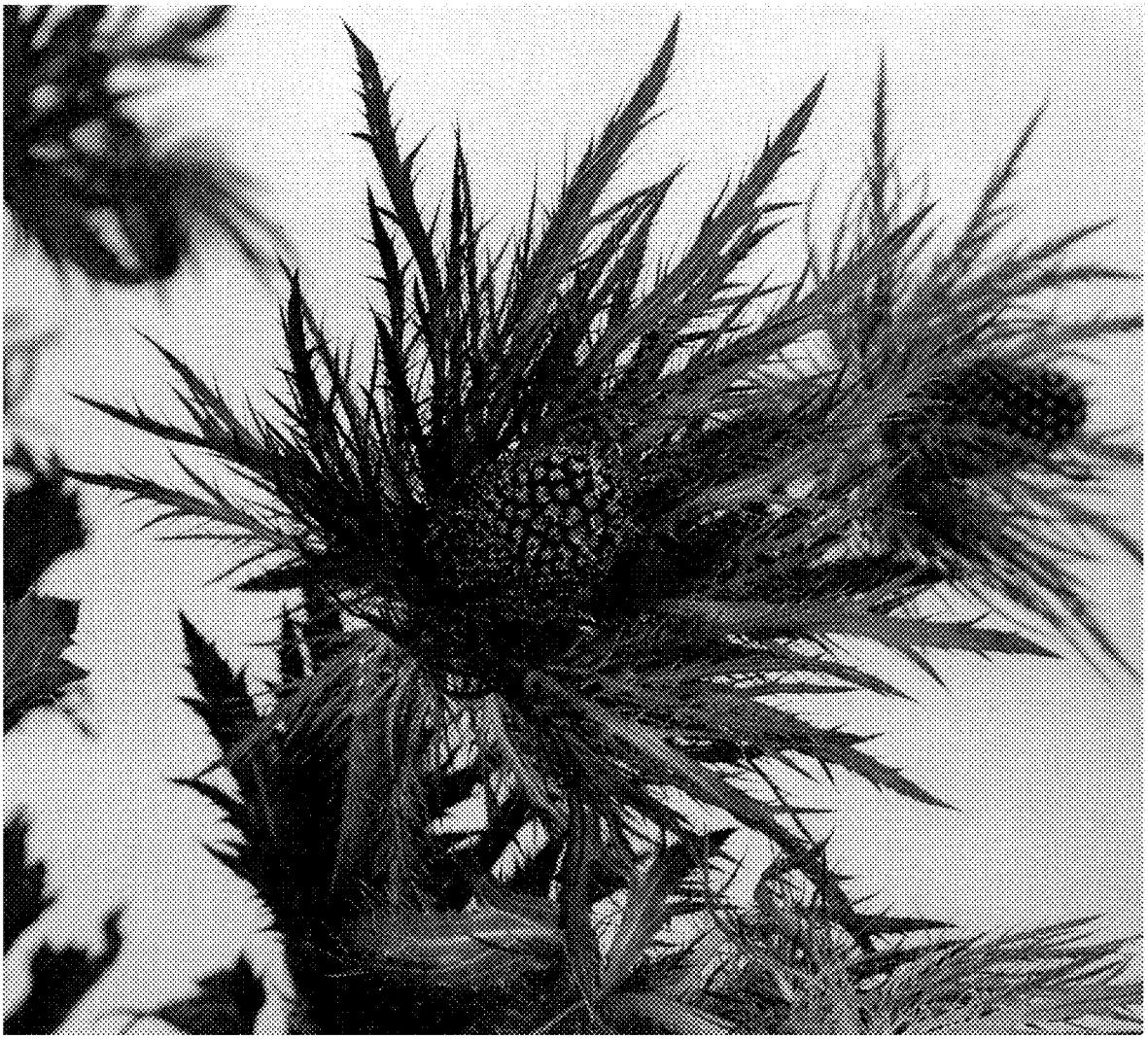
FIG. 3 shows, as nearly true as it is reasonably possible to make the same in color illustrations of this type, the typical inflorescence of 'LEGMAVI'.

The following is a detailed botanical description of a new and distinct variety of *Eryngium* plant known as 'LEGMAVI', based upon observations of 4-month-old plants grown in a sandy soil, outdoors, in Noordwijkerhout, the Netherlands. Plants were grown with full sun exposure, provided regular drip irrigation, and fertilized using fertigation techniques with an electroconductivity value of 1. Preventative fungicides were utilized for the control and suppression of *Alternaria* sp. diseases. Observation data was recorded in August of 2022.

A botanical description of 'LEGMAVI' and comparisons with the parents and most similar variety of common knowledge are provided below.

General plant description:

*Growth habit*.—Upright hermicryptophyte perennial with foliage borne in both a rosette and along the flowering stems.

*Plant profile*.—Narrowly triangular.

*Height*.—52.3 cm to the top of the foliar plane; 62.0 cm to the top of the floral plane.

*Spread*.—45.0 cm.

*Plant vigor*.—Moderately vigorous.

*Propagation*.—Method — Meristematic tissue culture. Time to initiate rooting — Approximately 10 to 14 days at an average ambient temperature of 22 degrees Celsius. Time to produce flowering plant from rooted cutting — Approximately 4 months in a 15 cm container.

*Pest resistance and susceptibility*.—Plants have not been observed to be any more or less susceptible or resistant to pathogens and pests known to affect *Eryngium* sp.

*Environmental tolerances*.—Adapt to, at least, USDA Zones 6 to 10 and temperatures ranging from minus 18 degrees Celsius to 35 degrees Celsius; moderate tolerance to rain; high tolerance to wind.

Root system:

*Description*.—Relatively deep taproot with a sparse network of thick, fleshy roots.

Stem:

*Branching habit*.—Main stems arising directly from the plant's base.

*Attitude*.—Upright and outward.

*Aspect*.—Rounded, with undeep axial ribs.

*Length*.—42.5 cm.

*Diameter*.—1.0 cm.

*Internode length*.—5.1 cm, on average; varying between 0.5 cm and 9 cm.

*Texture*.—Smooth.

*Pubescence*.—Glabrous.

*Luster*.—Moderately glossy.

*Strength*.—Strong.

*Color, juvenile*.—Yellow-green, nearest to RHS 144B; lightly to very strongly suffused with greyed-purple, nearest to RHS N186C.

*Color, mature*.—Yellow-green, nearest to RHS 146B; lightly to very strongly suffused with greyed-purple, nearest to RHS N186B.

*Color at internodes*.—Yellow-green, nearest to RHS 146B; lightly to very strongly suffused with greyed-purple, nearest to RHS N186B.

Foliage:

*Arrangement*.—Leaves are borne both basally and on the main stems; basal leaf arrangement is alternate and leaves on stems are arranged alternately as well.

*Basal leaves*.—Attachment — Petiolate. Division — Simple. Leaf shape — Broad ovate; unlobed. Dimensions —11.3 cm long, excluding the petiole, and 12.3 cm wide. Leaf attitude — Outward and upward. Leaf apex — Abruptly acute. Leaf base — Hastate; basal lobes free. Leaf margin — Dentate to serrate; moderate undulation. Texture, adaxial and abaxial surfaces — Slightly coriaceous. Pubescence, adaxial surface — Glabrous. Pubescence, abaxial surface — Glabrous. Luster, adaxial surface — Slightly glossy. Luster, abaxial surface — Slightly glossy. Color — Juvenile foliage color, adaxial surface — Green, nearest to RHS 137B. Juvenile foliage color, abaxial surface — Yellow-green, nearest to RHS 146A. Mature leaf color, adaxial surface — Green, nearest to RHS 137B. Mature leaf color, abaxial surface — Yellow-green, nearest to RHS 146A. Venation — Type — Lacinate. Vein color, adaxial surface — Yellow-green, nearest to in between RHS 145B and 145C. Vein color, abaxial surface — Yellow-green, nearest to RHS 148A. Petiole — Length — 3.5 cm. Diameter — 0.9 cm. Strength — Strong. Texture, adaxial and abaxial surfaces — Smooth and glabrous. Luster, adaxial surface — Very slightly glossy. Luster, abaxial surface — Moderately glossy. Color, adaxial surface — Nearest to a mixture of greyed-white and green-white, RHS 156B and 157A. Color, abaxial surface — Yellow-green, nearest to a mixture of RHS 145A, 145B, and 145C; greyed-red suffusion, nearest to RHS 182B, varies from not present on some petioles to very prominent on others.

*Cauline leaves*.—Attachment — Petiolate. Division — Simple. Leaf shape — Reniform to orbicular; deeply, pedately lobed. Lobes — Depth of sinuses — Deep. Sinus orientation — Divergent. Dimensions — 11.3 cm long, excluding the petiole, and 12.3 cm wide. Leaf attitude — Leaves in an average angle of 90 degrees to the stem. Leaf apex — Acute. Leaf base — Truncate. Leaf margin — Serrate. Texture, adaxial and abaxial surfaces — Slightly rugose; pubescent. Pubescence, adaxial surface — Moderately covered with short hairs with an average length of 0.2 mm; colored greyed-white, nearest to RHS 156D. Pubescence, abaxial surface — Sparsely covered with short hairs with an average length of 0.2 mm; colored greyed-white, nearest to RHS 156D. Luster, adaxial surface — Matte. Luster, abaxial surface — Slightly glossy. Color — Juvenile foliage color, adaxial surface — Green, nearest to RHS NN137C; lightly suffused with violet-blue towards the margin and apex, nearest to RHS N92D. Juvenile foliage color, abaxial surface — Yellow-green, nearest to a mixture of RHS 144A and 144B; lightly suffused with violet towards the margin and apex, nearest to RHS 88B. Mature leaf color, adaxial surface — Green, nearest to in between RHS NN137A and NN137B; suffused with violet-blue towards the margin and apex, nearest to RHS N89D. Mature leaf color, abaxial surface — Yellow-green, nearest to a mixture of RHS 144A and 146B. Venation — Type — Palmate. Vein color, adaxial surface — Greyed-white, nearest to RHS 156C, and fading to violet-blue towards the lobe tips, nearest to a mixture of RHS N89C and N89D. Vein color, abaxial surface — Yellow-green, nearest to RHS 148A, and lightly suffused with violet-blue, nearest to RHS N89C. Petiole — Length — 2.5 cm. Diameter — 0.5 cm. Strength — Strong. Texture, adaxial and abaxial surfaces — Smooth and glabrous. Luster, adaxial surface — Very slightly glossy. Luster, abaxial surface — Moderately glossy. Color, adaxial surface — Nearest to a mixture of greyed-white and greyed-green, RHS 156B and 157A. Color, abaxial surface — Yellow-green, nearest to RHS 145C.

Inflorescence:

*Habit*.—Compound umbel; typically with 3 oblong, capitular umbels which are each subtended by a prominent involucre.

*Natural flowering season*.—Mid-summer into autumn in the Netherlands.

*Time to flower or response time*.—Approximately 8 months from propagation, with recurrent flowering every 10 weeks during the flowering season.

*Overall height of the inflorescence*.—12.9 cm, including the involucre; 5.1 cm, excluding the involucre.

*Overall width of the inflorescence*.—16.0 cm, including the involucre; 2.6 cm, excluding the involucre.

*Quantity of flowers per inflorescence*.—480, on average.

*Peduncles*.—Length — Terminal peduncles are 11.4 cm on average. Diameter — Average of 0.5 cm. Angle — Lateral peduncles at an average angle of 50 degrees relative to the stem. Strength — Strong. Texture — Smooth and glabrous, with shallow ribs. Luster — Glossy. Color — Yellow-green, nearest to a combination of RHS 145A and 145B; lightly to very strongly suffused with violet-blue nearest to RHS 93A.

Flower buds:

*Shape*.—Oblong.

*Length*.—5.0 mm.

*Diameter*.—2.0 mm.

*Texture*.—Smooth and glabrous.

*Luster*.—Matte. Color — Yellow-green, nearest to RHS 145D; apex is violet-blue, RHS 96A, and suffused with yellow-green, nearest to RHS 147A.

Flower:

*Shape, type*.—Rotate, with a single whorl of petals; petals are free.

*Flowering habit*.—Freely flowering.

*Time to flower*.—Approximately 8 months from propagation.

*Flower longevity on plant*.—Approximately ten days.

*Persistent or self-cleaning*.—Persistent.

*Fragrance*.—Non-fragrant.

*Aspect*.—Upright to outward.

*Diameter*.—4.0 mm.

*Depth*.—7.0 mm.

*Petals*.—Quantity — 5. Arrangement — Rotate, with petals arranged in a single whorl; petals are free. Shape — Narrow obovate. Apex — Acute. Base — Narrow cuneate. Aspect — Strongly recurved. Dimensions — 3.0 mm long and 0.8 mm wide, as measured. Texture and luster, inner surface — Smooth, glabrous, and very slightly glossy. Texture and luster, outer surface — Smooth, glabrous, and very slightly glossy. Margin — Entire; no undulation. Color when opening, inner surface — Translucent white, nearest to RHS N155A. Main vein is violet-blue, nearest to RHS 96B. Color when opening, outer surface — Translucent white, nearest to RHS N155A. Main vein is violet-blue, nearest to RHS 96B. Color when fully opened, inner surface — Translucent greyed-white, nearest to RHS 156D, yet slightly lighter. Main vein is violet-blue, nearest to RHS 94C. Petals do not fade with age. Color when fully opened, outer surface — Translucent greyed-white, nearest to RHS 156D, yet slightly lighter. Main vein is violet-blue, nearest to RHS 94C. Petals do not fade with age.

*Pedicels*.—None. Flowers are sessile.

*Calyx*.—Shape — Rotate. Length — 0.4 cm. Diameter — 0.3 cm. Sepals — Arrangement — Rotate; one whorl of sepals. Quantity — 5 unfused sepals. Shape — Deltoid. Dimensions — 4.0 mm long and 2.0 mm wide. Apex — Pungent. Base — Cuneate. Margin — Entire; no undulation. Texture and luster, upper surface — Smooth, glabrous, and very slightly glossy. Texture and luster, lower surface — Smooth, glabrous, and very slightly glossy. Color — When opening, upper surface — Violet-blue, nearest to RHS 96A, and strongly suffused with yellow-green, nearest to RHS 147D yet slightly darker. When opening, lower surface — Violet-blue, nearest to RHS 96A, and moderately suffused with yellow-green, nearest to RHS 147D yet slightly darker. Fully opened, upper surface — Blue, nearest to RHS 103B, and moderately suffused with greyed-green, nearest to RHS N189A. Fully opened, lower surface —Blue, nearest to RHS 103B, and lightly suffused with greyed-green, nearest to RHS N189A. Venation — Fully opened, upper surface — Yellow-green, nearest to RHS 144A. Fully opened, lower surface — Greyed-purple, nearest to RHS 183B.

*Floral bract*.—Position — A single bract is present at the base of each individual flower. Shape — Lanceolate. Length — 5.0 mm. Width — 0.5 mm. Apex — Narrow acuminate. Base — Narrow cuneate. Margins — Entire; occasionally with a single Color, adaxial surface — Blue, nearest to RHS 103D. Color, abaxial surface — Blue, nearest to RHS 103D. Texture, adaxial surface — Smooth; glabrous. Texture, abaxial surface — Smooth; glabrous.

*Involucre*.—Position — A prominent involucre, with four whorls of bracts, is present at the base of each corymb. Quantity of bracts — Approximately 60. Shape — Obovate to oblanceolate and lanceolate. Length — 7.6 cm, on average; varying between 2.6 cm and 11.2 cm. Width — 2.8 cm, on average; varying between 0.6 cm and 4.8 cm. Apex — Narrow acuminate. Base — Cuneate. Margins — Serrate; deeply incised. Color, adaxial surface — Violet-blue, nearest to a mixture of RHS 90A and 90B; suffused with yellow-green, nearest to a mixture of RHS 147B and 147D. Main vein is violet-blue, nearest to RHS 90A yet darker. Color, abaxial surface — Green, nearest to RHS 137C. Veined violet-blue, nearest to RHS N92D. Texture, adaxial surface — Smooth; glabrous. Texture, abaxial surface — Smooth; glabrous.

Reproductive organs:

*Androecium*.—Stamens — Quantity — 5. Anthers — Attachment — Dorsifixed. Shape — Oblong. Dimensions — 1.0 mm long and 0.5 mm wide. Color — Violet-blue, nearest to RHS N92A. Filaments — Length — 2.0 mm. Color — Violet-blue, nearest to RHS N92A. Amount of Pollen — Sparse. Pollen color — White, nearest to RHS 155A.

*Gynoecium*.—Pistil — Quantity — 2. Length — 4.0 mm. Style — Length — 3.75 mm. Color — Violet-blue, nearest to RHS 94B, and fading to yellow-green towards the base, nearest to RHS 145D. Stigma — Shape — Club-shaped. Diameter — 0.2 mm. Color — Violet-blue, nearest to RHS 94B. Ovary Color — Yellow-green, nearest to RHS 145D.

Seed and fruit: No fruit or seeds have been observed to date.

COMPARISONS WITH THE PARENT PLANTS

Plants of the new cultivar 'LEGMAVI' differ from its presumed parents, unnamed *Eryngium alpinum* plants (not patented) which typify the species, by the characteristics described in Table 1.

TABLE 1

| Characteristic | 'LEGMAVI' | The presumed parents. |
|---|---|---|
| Vernalization requirement. | None. | Requires vernalization to induces growth of flowering stems. |
| Bloom habit. | Continuous flowering. | Flowers once a season. |
| General coloration of the cauline leaf nearest to the involucre. | Green and heavily suffused with violet-blue. | Green and lightly suffused with violet-blue. |
| General coloration of the flower eye. | Darker purple by comparison to the seed parent. | Lighter purple by comparison to 'LEGMAVI'. |
| Length of stems. | Longer than the parent. | Shorter than 'LEGMAVI'. |
| General coloration of the umbels. | A darker shade of blue relative to the parent. | A lighter shade of blue relative to 'LEGMAVI'. |

COMPARISON WITH THE MOST SIMILAR VARIETY OF COMMON KNOWLEDGE

Plants of the new cultivar 'LEGMAVI' may be distinguished from the most similar known commercial comparator, *Eryngium alpinum* 'Blue Star' (not patented), by the characteristics described in Table 2.

TABLE 2

| Characteristic | 'LEGMAVI' | 'Blue Star' |
|---|---|---|
| Vernalization requirement | None. | Requires vernalization to induces growth of flowering stems. |
| Bloom habit. | Continuous flowering. | Flowers once a season. |
| General coloration of the cauline leaf nearest to the involucre. | Green and heavily suffused with violet-blue. | Green and lightly suffused with violet-blue. |
| General coloration of the flower eye. | Darker purple by comparison to the seed parent. | Lighter purple by comparison to 'LEGMAVI'. |
| Length of stems. | Longer than 'Blue Star'. | Shorter than 'LEGMAVI'. |
| General coloration of the umbels. | A darker shade of blue relative to 'Blue Star'. | A lighter shade of blue relative to 'LEGMAVI'. |

That which is claimed is:

1. A new and distinct variety of *Eryngium alpinum* plant named 'LEGMAVI', substantially as described and illustrated herein.

* * * * *